(12) United States Patent
Villa et al.

(10) Patent No.: US 6,187,936 B1
(45) Date of Patent: Feb. 13, 2001

(54) PROCESS FOR THE ENZYMATIC KINETIC RESOLUTION OF 3-PHENYLGLYCIDATES BY TRANSESTERIFICATION WITH AMINOALCOHOLS

(75) Inventors: Marco Villa, Milan; Dario Tentorio, Vigano' ; Angelo Restelli, Gerenzano; Sergio Riva, Seveso, all of (IT)

(73) Assignee: Zambon Group S.p.A., Vicenza (IT)

( * ) Notice: Under 35 U.S.C. 154(b), the term of this patent shall be extended for 0 days.

(21) Appl. No.: 09/399,962

(22) Filed: Sep. 20, 1999

(30) Foreign Application Priority Data

Sep. 24, 1998 (IT) ............................................. MI98A2061

(51) Int. Cl.⁷ ..................... C07D 303/40; C07D 281/02; C07D 285/36
(52) U.S. Cl. ............................................. 549/549; 540/491
(58) Field of Search ............................. 549/549; 540/491

(56) References Cited

U.S. PATENT DOCUMENTS 5,571,704    11/1996    Ghirotto et al. ..................... 435/123

FOREIGN PATENT DOCUMENTS

| 0 127 882 A1 | 12/1984 | (EP) . |
| 0 158 340 A2 | 10/1985 | (EP) . |
| 0 498 706 A1 | 6/1992 | (EP) . |
| 0 498 706 | 8/1992 | (EP) . |
| 0 602740 | 6/1994 | (EP) . |
| 0 860439 | 8/1998 | (EP) . |
| 1 236 647 1A | 6/1971 | (GB) . |
| 2 167 063 | 5/1986 | (GB) . |
| 2 246 351 | 1/1992 | (GB) . |

OTHER PUBLICATIONS

Paolo Crotti et al., "Ring–Opening Reactions of cis– and trans–2,3–Bis (4–methoxybenzyl) oxirane: Competition between Assistance by and Migration of an Aryl Group", *J. Orig. Chemical*, 1986, vol. 51, pp. 2759–2766.

Da–Ming Gou et al., "A Practical Chemoenzymatic Synthesis of the Taxol C–13 Sid Chain N–Benzoyl–(2R, 3S)–3–phenylisoserine", *J. Orig. Chemical*, 1993, vol. 58, pp. 1287–1289.

Aleksey Zaks et al., "Application of biocatalysis and biotransformations to the synthesis of pharmaceuticals", *Drug Discovery Today*, vol. 12, No. 12, Dec. 1997.

George M. Whitesides, "Enzymes as Catalysts in Synthetic Organic Chemistry", *Agnew Chem. Int. Ed. Engl.*, vol. 24, (1985) pp. 617–638.

Alexander M. Klibanov, "Asymmetric Transformations Catalyzed by Enzymes in Organic Solvents", *Acc. Chem. Res.* 1990, vol. 23, pp. 114–120.

"The Merck Index", *Merck Research Laboratories*, 12th Edition, 1996, pp. 541 and 1200.

"Manufacture of optically active glycidic acid esters with esterase and preparation of diltiazem from the glycidic acid esters", *16–Fermentations*, vol. 121, 1994, pp. 877.

Primary Examiner—Ba K. Trinh
(74) Attorney, Agent, or Firm—Arent, Fox Plotkin & Kahn

(57) ABSTRACT

A process for the preparation of I:

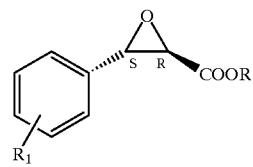

(I)

in which R and R1 have the meanings reported in the description, that comprises the enzymatic kinetic resolution by transesterification with aminoalcohols of 3-phenylglycidates of formula I:

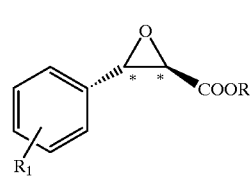

trans (I)

is described.

17 Claims, No Drawings

PROCESS FOR THE ENZYMATIC KINETIC RESOLUTION OF 3-PHENYLGLYCIDATES BY TRANSESTERIFICATION WITH AMINOALCOHOLS

The present invention relates to a process for the resolution of 3-phenylglycidates and, more particularly, it relates to a process for the enzymatic kinetic resolution of 3-phenylglycidates by transesterification with aminoalcohols.

The esters of 3-phenylglycidic acid are known compounds, described in the literature and widely used as synthetic intermediates.

For example esters of trans-3-phenylglycidic acid, appropriately resolved, are commonly used for the preparation of (2R,3S)-N-benzoyl-3-phenylisoserine, side chain of paclitaxel, a known anticancer drug of natural source (Merck Index, XII edition, n. 7117, page 1200).

Another significant use of 3-phenylglycidates, and in particular of (2R,3S)-3-(4-methoxyphenyl)glycidates, is for the synthesis of the compound (+)-(2S,3S)-3-acetoxy-5-(2-dimethylaminoethyl)-2,3-dihydro-2-(4-methoxyphenyl)-1,5-benzothiaze pin-4(5H)-one, a known drug with calcium-blocker activity named Diltiazem (Merck Index, XII edition, n. 3247, page 541).

The preparation of Diltiazem, starting from esters of 3-(4-methoxyphenyl)glycidic acid, can be performed according to several literature methods, for example according to the processes claimed in the British patents N° 1236467 and 2167063 or in the European ones N° 127882 and 158340, all in the name of Tanabe Seyaku Co. Ltd.

In order to prepare Diltiazem it is necessary to accomplish an optical resolution on one of the intermediates of the synthesis. Obviously the resolution performed at an initial step of the process is economically more convenient in that the economic value of the product subjected to resolution is lower and as a consequence the discharged isomer does not represent a relevant loss.

Therefore it is advantageous to have esters of 3-(4-methoxyphenyl)glycidic acid in enantiomeric pure form in that said compound is the first optically active intermediate of the synthesis.

Most procedures reported in the literature for the preparation of 3-phenylglycidates yields racemic mixtures. It is possible mainly to obtain one of the two possible couples of enantiomers for example the trans racemate (2R*,3S*) as in the case of the Darzens condensation between 4-methoxybenzaldehyde and methyl chloroacetate [J.Org.Chem.,(1986), 51,2759] by suitably choosing the synthetic route and optimising the experimental conditions.

Nevertheless even disposing of the single couple of trans enantiomers it results anyway necessary to isolate the desired enantiomer, with a 2R,3S absolute configuration in the specific case of 3-(4-methoxyphenyl)glycidates used for Diltiazem synthesis, or the 2R,3S or 2S,3R enantiomer depending on the synthetic route in the case of 3-phenylglycidates used for the preparation of the side chain of paclitaxel [J.Org.Chem.,(1993), 58, 1287], resorting to resolution techniques.

Apart the more conventional procedures of resolution, that consist of transforming the racemic mixture into a diasteroisomeric mixture by interaction with an enantiomerically pure resolving agent and subsequently by separating such a mixture by classical methodologies, such as for example chromatographic purifications or fractional crystallisations, the kinetic resolution techniques are really attractive.

On the contrary, such resolution techniques are based on the different reaction rate of each enantiomer with respect to optically active reagents or to achiral reagents but in the presence of chiral catalysts.

A particularly important group of chiral catalysts is constituted by enzymes, whose use as resolving agents has only recently been recognised and developed [A. Zaks et al. in Drug Discovery Today, (1997), 2, 513].

Many enzymatic processes for the resolution of carboxylic acids and related esters are described in the literature, see for example the Reviews published on Angew.Chem., Int.Ed.Eng.(1985), 24, 617 and (1989), 28,695.

Within this domain the processes that make use of hydrolitic enzymes, such as lipases and proteases in non-aqueous media, for the kinetic resolution of esters by transesterification reaction [A. Klibanov in Acc. Chem. Res. (1990), 23, 114], for example according to the following scheme:

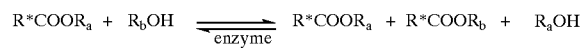

are particularly interesting.

In the best conditions it is possible preferentially to transesterify only one of the two enantiomers, thus differentiating it from the other, and then to resolve the racemic mixture with nearly quantitative yields.

In the above mentioned processes the choice of the alcohol $R_bOH$ is crucial, in that it must ensure to the new formed ester completely different chemical-physical properties in comparison with the starting compound, thus facilitating the separation procedures of the two esters, for example by chromatography, preferential crystallisation, distillation or salification.

Some resolution processes of racemic phenylglycidates by enzymatic transesterification techniques are reported in the literature.

A first example of resolution of racemic 3-(4-methoxyphenyl)glycidates by enzymatic transesterification is described in the patent application GB 2246351, in the name of the same applicant.

A similar approach is used by Da-Ming Gou et al in J.Org.Chem. (1993), 58, 1287 for the synthesis of the side chain of paclitaxel. The authors describe the resolution of trans methyl 3-phenylglycidate by transesterification reaction, catalysed by the lipase from *Mucor miehei*, with isobutyl alcohol.

The final isolation of the single enantiomers is performed by chromatography or by fractional distillation, that is by employing procedures commonly used for laboratory scale but not easily applied at industrial level.

A similar process of kinetic resolution of phenylglycidates catalysed by esterases, in which the alcohol used in the transesterification reaction is a $C_2$–$C_{10}$ alkanohol, is reported by Tanabe in JP 06/078790. Even if it allows the obtainment of the desired product, that is the already mentioned (2R,3S)-3-(4-methoxyphenyl)glycidate precursor of Diltiazem, with a high degree of optical purity, the method is not easily applicable at industrial level in that it exploits chromatographic techniques for its isolation.

On the contrary, a different approach, described in the European patent application N° 498706 (Synthelabo), that suggests an alternative route to overcome the above mentioned problems of isolation of the single enantiomers, is based on the stereoselective insolubilization of a single enantiomer by transesterification: the enzymatic transesterification reaction performed on the racemic trans methyl 3-(4-methoxyphenyl)glycidate in the presence of sodium 4-hydroxybutyrate leads to the formation of the insoluble carboxyester of the (2S,3R) enantiomer. The desired enantiomer (2R,3S) is recovered by filtration and evaporation of the filtrate.

Nevertheless by working under concentrated conditions, preferable from the industrial point of view, the toluene reaction mixture turns out to be particularly thick also for the presence out of phase of the insoluble (2S,3R) carboxyester and sodium hydroxybutyrate, in addition to the enzyme: the precipitation of these solids on the enzymatic surface unavoidably reduces its activity and make its recovery difficult. With the aim to improve the filterability properties of the suspension it is necessary to work under rather diluted conditions, for example using 3% w/v solutions, as described in example 1 of the above mentioned patent, all at detriment of the process productivity. For the above reported reasons the process claimed by Synthelabo is hardly applicable in industry.

In our knowledge, a process for the enzymatic kinetic resolution of 3-phenylglycidates by transesterification with aminoalcohols of simple industrial applicability and with remarkably simplified isolation procedures of the desired enantiomer has never been described in the literature.

We have now found a process for the enzymatic kinetic resolution of enantiomeric mixtures of 3-phenylglycidates particularly suitable for the industrial application, by transesterification with aminoalcohols, in non-aqueous conditions, of the enantiomeric mixture of esters and subsequent separation of the transesterified ester from the non-transesterified one by extraction with an acid medium.

Therefore object of the present invention is a process for the preparation of:

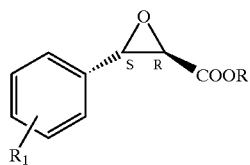

(I)

which comprises the enzymatic kinetic resolution of trans 3-phenylglycidates of formula:

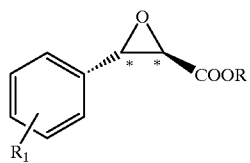

trans (I)

wherein

R is linear or branched $C_1$–$C_4$ alkyl;

$R_1$ is hydrogen, linear or branched $C_1$–$C_3$ alkyl, linear or branched $C_1$–$C_3$ alkoxy, aryl or halogen;

by transesterification of the mixture of trans enantiomers of formula I catalysed by enzymes in organic solvent with aminoalcohols of formula:

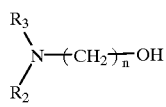

(II)

wherein n is an integer from 2 to 4;

$R_2$ is hydrogen or linear or branched $C_1$–$C_4$ alkyl;

$R_3$ is linear or branched $C_1$–$C_4$ alkyl; or $R_2$ and $R_3$, together with the nitrogen atom form a 5 to 7 membered saturated cycle;

to give a mixture of trans esters, non transesterified and transesterified, having an opposite absolute configuration, of formula III and IV respectively:

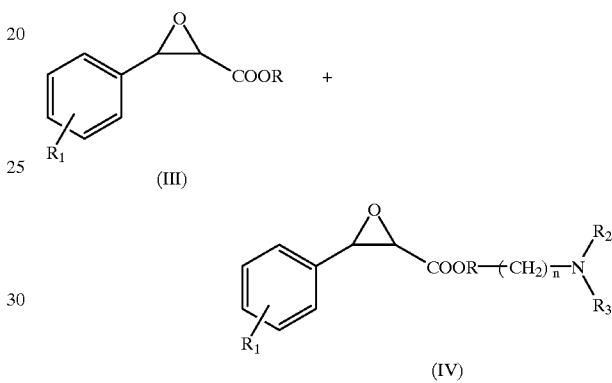

wherein R, $R_1$, $R_2$, $R_3$ and n have the above reported meanings, and the subsequent separation of such a mixture of esters of formula III and IV.

The process object of the present invention is easily performed and allows to obtain the single enantiomers of racemic esters of formula I with good yields and high enantiomeric excesses, avoiding troublesome procedures of purification, with harmless and commercially available reagents.

The transesterification reaction according to the process object of the present invention is performed by reaction between a trans racemic ester of formula I and an aminoalcohol of formula II in the presence of a suitable enzyme, in non-aqueous medium.

The racemic trails esters of formula I are known compounds, easily prepared for example according to the already cited Darzens condensation starting from optionally substituted benzaldehydes and from the corresponding 2-haloacetates [J.Org.Chem., (1986), 51, 2759].

Examples of esters of formula I usable in the present process of resolution are methyl, ethyl and propyl ester.

Methyl ester is particularly preferred.

According to the process object of the present invention the transesterification reaction occurs in the presence of an aminoalcohol of formula II.

Examples of aminoalcohols of formula II utilisable in the process object of the present invention are 3-dimethylamino-1-propanol, 2-diethylaminoethanol, 2-dimethylaminoethanol, 2-methylaininoethanol, 1-(2-hydroxyethyl)piperidine, 1-(2-hydroxyethyl)pyrrolidine.

2-Dimethylaminoethanol, a compound easy to be found, scarcely toxic, liquid at room temperature and stable, is particularly preferred.

In the enzymatic resolution process object of the present invention the aminoalcohol of formula II is used in a molar ratio comprised between 20:1 and 0.4:1 with respect to the ester of formula I.

Preferably such a molar ratio is comprised between 10:1 and 1:1, even more preferably it is 2:1.

The enzymes useful for the purpose can be of different kind.

In particular lipases of animal, microbial or vegetable origin can be used, as for example lipase from *Candida antarctica*, lipase from *Mucor miehei*, pancreatic porcine lipase, lipase from *Candida cylindracea*, lipase from wheat germ, lipase from *Chromobacterium viscosum*, lipase from *Aspergillus niger*, lipase from *Rhizopus javanicus*, lipase from *Pennicillium cyclopium*, lipase from *Rhizopus delemar*, lipase from *Candida lipolytica*, lipase from *Pennicilium roquefortii*, lipase from *Humicola lanuginosa*, lipase from *Geotrichum candidum*, lipase from *Pseudomonas cepacea*, lipase from *Rhizopus japonicus* and lipase from *Pseudomonas fluorescens*, optionally supported.

The supported lipase from *Candida antarctica*, named Novozim 435® (Novo Nordisk), the lipase PS from *Pseudomonas cepacea* supported on celite (Amano), the type II pancreatic porcine lipase (Sigma) and the lipase CE5 from *Humicola laniginosa* (Amano) are particularly preferred.

The supported lipase from *Candida antartica*, named Novozim 435®, for its features of high enantioselectivity, stability and easy availability, is even more preferred The enzyme employed in the process object of the present invention can be recovered at the end of the reaction and used again many times, without loss of activity.

The enzymatic transesterification reaction object of the present invention is performed into a non-aqueous medium.

Organic solvents usable as reaction solvents are for example aromatic solvents, such as benzene, chlorobenzene, xylene or toluene, hydrocarbons such as n-hexane, cyclohexane or n-heptane, ethers such as diethylether, diisopropylether, terbutylmethylether, tetrahydrofuran or dioxane, ketones such as methylethylketone or acetone, alcohols such as ter-butanol or 2-methyl-2-butanol, aprotic dipolar solvents such as acetonitrile or chlorinated solvents such as inethylene chloride or admixtures thereof.

For practical reasons toluene is preferably used.

The transesterification reaction object of the present invention can be a reversible reaction, in particular when the leaving alcohol ROH has a high nucleophilicity. With the aim to move the reaction equilibrium towards the desired direction many strategies can be adopted, for example esters of formula I in which the R residue comes from low nucleophilic alcohols, bearing electronwithdrawing groups in $\alpha$ or $\beta$ position, or of vinyl type, that afford non-reactive carbonyl species, or anhydrides of formula I in which R represents an acyl residue, can be used.

Therefore the use of esters in which R for example represents a 2-fluoroethyl, 2,2,2-trifluoroethyl, 2-chloroethyl, 2,2,2-trichloroethyl, cyanomethyl, 2-nitropropyl, vinyl and an isopropenyl residue or an acyl residue such as formyl, acetyl or propionyl is also within the scope of the present invention.

On the contrary an alternative approach consists in increasing the concentration of the aminoalcohol of formula II or in removing the alcohol ROH released during the transesterification process. The removal of the alcohol ROH can be performed with several techniques, for example by absorption on inert materials or by distillation at reduced pressure, preferably by azeotropic distillation.

Particularly preferred is the removal of the alcohol ROH by azeotropic distillation. Examples of inert materials usable for absorbing alcohols are the molecular sieves, preferable the 5 Å molecular sieves in the case of methanol (Union Carbide Type 5 Å, ⅛" rods, Fluka).

The azeotropic removal of the alcohol ROH can be accomplished by adding a suitable amount of a second solvent, selected according to the kind of alcohol to be removed, to the reaction medium. This second solvent, together with the alcohol ROH and optionally with the reaction solvent and the aminoalcohol too, yields an azeotropic system having a boiling point lower than the one of the alcohol ROH itself. In this way, by removing the azeotrope by mild heating and under reduced pressure and by restoring the optionally evaporated aminoalcohol, it is possible to favour the shifting of the reaction equilibrium without using drastic experimental conditions, incompatible with the chemical stability of the substrates and with the maintenance of a high enzymatic enantioselectivity.

For example in the case in which the alcohol ROH is methanol, the second solvent usable for making the azeotrope can be methylcyclohexane.

An important parameter in the process object of the present invention is the reaction temperature, in that it affects not only the rate but also the enantioselectivity of the enzymatic system.

Generally it operates at the temperature that allows the highest solubilisation of the substrates and the removal of the optional azeotropic system by distillation, together with an ideal enzymatic activity.

For example the usable temperature range can vary from 5 to 50° C., at ambient pressure or under vacuum. Preferably it operates between 10 and 30° C., even more preferably at room temperature.

In the process object of the present invention the phase of isolation of the reaction products is particularly handy and easy to be realised.

Generally it proceeds by removing the supported enzyme and the optional molecular sieves by filtering and by extracting the filtrate first with water, in order to eliminate the excess of hydrosoluble aminoalcohol of formula II, and then with an acid aqueous phase: the transesterified product of formula IV and the non-transesterified one of formula III will be in the acid aqueous phase and in the organic one respectively.

The acid washings are performed by using aqueous solutions of organic or inorganic acids, such as for example acetic, hydrochloric, sulfuric, phosphoric acid or sulfonic acid under such concentrations and conditions of addiction to guarantee a pH of the medium sufficient to salify the amine function and that is compatible with the chemical stability of the desired enantiomer.

Once partitioned the mixture of esters of formula III and IV between the organic phase and the acid aqueous phase respectively it can then proceed to the recovery of the product of formula III from the organic phase by simple evaporation.

The so obtained raw product has such an optical purity to allow, for example, its direct use for the preparation of Diltiazem according to synthetic processes already described in the literature, without needing further work-out and purifications.

On the contrary it is possible to further increase the enantiomeric excess of the so isolated raw ester by subsequent crystallisation by seeding the suitable saturated solution with crystals of the homochiral compound.

The resolution process object of the present invention is based on the different reaction rate of the two enantiomers under conditions of enzymatic catalysis: the enantiomer that will preferably undergo the transesterification reaction can differ according to the kind of enzyme used.

For example starting from the racemic trans mixture of methyl 3-(4-methoxyphenyl)glycidate and in the presence of the supported lipase from *Candida antarctica* (Novozim 435®) the enantiomer (2S,3R) is preferably transesterified, while the antipode (2R,3S), useful intermediate for the synthesis of Diltiazem, remains unchanged. In such a case the useful enantiomer will be recovered by evaporation of the organic phase.

In a preferred embodiment of the process object of the present invention, the lipase and the aminoalcohol of formula II are added to the solution of the racemic trans ester of formula I in the suitable organic solvent and in the presence of the co-solvent selected for making the azeotrope, at room temperature. The suspension is kept under stirring and under azeotropic distillation conditions, suitably restoring the solvent, the co-solvent and the aminoalcohol, for the time necessary for the completion of the transesterification and then filtered. The so recovered enzyme is washed with an organic solvent and used again for subsequent reactions. The filtrate is first washed with water then with the acid solution up to a complete removal of the aminoester of formula IV, evaporated to dryness to yield the raw homochiral ester of formula III, that can optionally be crystallised by seeding with an optically pure sample of ester of formula III or used as such.

The process object of the present invention is easy to be realised and allows to obtain the homochiral glycidic esters of formula I with good yields and high enantiomeric excesses.

The starting esters of formula I can be smoothly prepared as an almost exclusively trans mixture of enantiomers by Darzens reaction. This allows to perform the subsequent enzymatic resolution directly on the reaction crude, avoiding additional procedures of purification.

The mild reaction conditions, and in particular the use of non-aqueous solvents and of restrained temperature, make the process particularly suitable for the esters of 3-phenylglycidic acid, substrates characterised by a high instability. In effect the experimental conditions of the present process are such to minimise the hydrolytic cleavage reactions of the epoxidic ring of the desired enantiomer, allowing a good recovery.

In addition the considerable solubility of phenylglycidates in the organic phase and the absence of formation of solids during the reaction allow to perform the present process in concentrated organic solutions and therefore ensure a higher productivity with respect to the already cited process described in the European patent application N° 498706 (Synthelabo), making the process object of the present invention particularly suitable for the industrial application.

Another interesting aspect of the present process is the use of particularly stable enzymes, handy and recoverable at the end of the reaction by simple filtration, that retain a good enzymatic activity and that can therefore be used again for several productive cycles.

At last an important advantage of the process object of the present invention is the considerably simplified final procedure of isolation of the desired enantiomer: the final separation of the enantiomers, which exploits the presence of the basic function acquired during the transesterification process and that allows the practically quantitative recovery of the desired ester, in effect presents a great practical interest in that extremely handy, versatile and cheaper than alternative techniques such as chromatographies or distillations.

In addition the restrained conditions of pH used in the separation process are perfectly compatible with the low stability of acid-sensitive substrates such as the esters of 3-phenylglycidic acid in object.

In conclusion, the use of mild reaction conditions, and in particular the use of non-aqueous solvents, the utilisation of particularly stable enzymes, handy and recoverable at the end of reaction, the handling of simple aminoalcohols such as for example 2-dimethylaminoethanol, the remarkably simplified final procedure of isolation of the single enantiomers, the high productivity and the obtainement of homochiral 3-phenylglycidates with good yields and high enantiomeric excesses make the process object of the present invention particularly suitable for the industrial application.

With the aim to illustrate the present invention, nevertheless without limiting it, the following examples are now given.

EXAMPLE 1

Resolution of Racemic Trans methyl 3-(4-methoxyphenyl)glycidate by Enzymatic Transesterification With 2-dimethylaminoethanol Changing the Enzyme Some transesterification trials on racemic trans methyl 3-(4-methoxyphenyl)glycidate with 2-dimethylaminoethanol using different lipases, in particular the supported lipase from *Candida antarctica*, named Novozim 435® (450U/100 mg of dry product, Novo Nordisk), the PS lipase from *Pseudomonas cepacea* supported on celite (375U/50 mg of dry product, Amano), the type II lipase from porcine pancreas (1330U/100 mg of dry product, Sigma) and the CE5 lipase from *Humicola lanuginosa* (550U/100 mg of dry product, Amano) were performed. The enzymatic enantioselectivity E was calculated according to the following Sih's formula [see J.Am.Chem. Soc. (1982), 104, 7294]:

$$E = \frac{\ln[(1-c)(1-ee_s)]}{\ln[(1-c)(1+ee_s)]}$$

in which c represents the conversion extent, while $ee_s$ the enantiomeric excess of the remaining substrate.

The reactions were performed by dissolving the racemic trans methyl 3-(4-methoxyphenyl)glycidate (21 mg, 0.1 mmoles) in ter-butylmethylether (0.8 ml) and by adding 2-dimethylaminoethanol (0.2 ml, 2 mmoles) and the commercial enzymatic preparation (10/50/100 mg) to the solution; the obtained suspension was left at room temperature and under stirring for the time reported in the table.

The conversion extent c and the enatiomeric excess $ee_s$ of the reactions were evaluated by HPLC analysis under the following analytical conditions (table I):

TABLE 1

HPLC analytical conditions

|   | Column | Eluant | Efflux ml/min | Detector | λ nm | Retention time Min. | |
|---|---|---|---|---|---|---|---|
| c | Whatman Partisil 5 (silica) | petrolatum/ ethyl acetate/ diethylamino ethanol 95/5/0.5 | 1.2 | UV Jasco 875 | 260 | 10.15 Me-PGA | 19.10 DMAE-PGA |
| $ee_s$ | Chiralcel OD (Daicel Chem. Ind) | petrolatum/ isopropanol 93/7 | 0.5 | UV Jasco 875 | 260 | 20.8 (2R,3S) Me-PGA | 28.9 (2S,3R) Me-PGA |

Me-PGA: methyl 3-(4-methoxyphenyl)glycidate;
DMAE-PGA: dimethylaminoethyl 3-(4-methoxyphenyl)glycidate The analytical samples were prepared by drawing a part of the reaction, filtering, suitably diluting the organic solution by adding a 95:5 mixture of petrolatum:ethyl acetate and afterwards washing with a 0.05M acetic acid/sodium acetate buffer solution at pH=5. The organic phase separated and dried on sodium sulphate was directly used for the HPLC analysis.

The used specific experimental conditions and the obtained results are summarised in the following table II:

TABLE II resolution of racemic trans methyl 3-(4-methoxyphenyl)glycidate changing the enzyme

| Enzyme (mg) | Source | Time (h) | c % | $ee_s$ % | E |
|---|---|---|---|---|---|
| Novozim 435 ® (10) (supported) | Candida antarctica | 2.5 | 52.11 | 72.68 | 10.70 |
| PS lipase (50) (supported) | Pseudomonas cepacea | 2 | 25.39 | 20.95 | 5.14 |
| type II lipase (100) | porcine pancreas | 24 | 17.09 | 17.23 | 13.24 |
| CE5 lipase (100) | Humicola lanuginosa | 25 | 34.88 | 44.86 | 17.56 |

In the reported examples the 2S,3R enantiomer was preferably transesterified, while the enantiomer useful for Diltiazem synthesis remained unchanged. From the data reported in the table it appears that the used enzymes show good characteristics of enantioselectivity.

EXAMPLE 2

Resolution of Racemic Trans methyl 3-(4-methoxyphenyl)glycidate by Enzymatic Transesterification With 2-dimethylaminoethanol Changing the Solvent According to a procedure similar to the one reported in example 1, some transesterification trials of racemic trans methyl 3-(4-methoxyphenyl)glycidate with 2-dimethylaminoethanol in the presence of Novozim 435®, at room temperature, by using different solvents, beginning from the following starting materials:

racemic trans methyl 3-(4-methoxyphenyl)glycidate (21 mg, 0.1 mmoles)

2-dimethylaminoethanol (0.2 ml, 2 mmoles)

solvent (0.8 ml)

Novozim 435® (10 mg)

were performed.

The values of c and $ee_s$ calculated on the basis of the HPLC analysis performed according to the procedure reported in example 1, are ordered in the following table:

TABLE III resotution of racemic trans methyl 3-(4-methoxyphenyl)glycidate changing the solvent

| Solvent | c % (2 h) | $ee_s$ % | B |
|---|---|---|---|
| ter-butylmethylether | 49.22 | 69.90 | 12.51 |
| toluene | 44.90 | 64.16 | 16.16 |
| xylene | 42.60 | 60.44 | 18.00 |
| 2-methyl-2-butanol | 49.53 | 68.92 | 11.61 |
| ter-butanol | 57.07 | 78.57 | 8.98 |
| tetrahydrofuran | 35.08 (35 h) | 43.19 | 13.66 |
| dioxane | 22.31 | 24.81 | 17.44 |
| acetonitrile | 31.70 | 36.55 | 11.99 |
| acetone | 21.73 | 23.96 | 17.17 |

From the E reported values it can be notice that substantial differences of the enzymatic performance by changing the used solvent do not exist.

EXAMPLE 3

Resolution of Racemic Trans methyl 3-(4-methoxyphenyl)glycidate by Enzymatic Transesterification Changing the Aminoalcohol According to a procedure similar to the one reported in example 1, some trials of transesterification of racemic trans methyl 3-(4-methoxyphenyl)glycidate with Novozim 435®, in toluene and at room temperature, using different aminoalcohols, beginning from the following starting materials:

racemic trans methyl 3-(4-methoxyphenyl)glycidate (Me-PGA)

aminoalcohol toluene

Novozim 4350® molecular sieves 5 Å were performed.

The values of c and $ee_s$ calculated on the basis of the HPLC analysis performed according to the procedure reported in example 1, are ordered in the following table IV:

TABLE IV resolution of racemic trans methyl 3-(4-methoxyphenyl)glycidate changing the aminoalcohol

| Me-PGA (mg) | Aminoalcohol | Toluene (ml) | Novozim 435 ® (mg) | Molec. sieves 5 Å (mg) | Time (h) | c % | $Ee_s$ % | E |
|---|---|---|---|---|---|---|---|---|
| 200 | 1-(2-hydroxyethyl) piperidine (0.2) | 0.8 | 20 | 500 | 3 | 51.96 | 65.28 | 7.76 |
| 200 | 2-diethylamino ethanol (0.2) | 0.8 | 20 | 500 | 3 | 59.85 | 76.84 | 6.94 |
| 200 | 1-(2-hydroxyethyl) pyrrolidine (0.2) | 0.8 | 20 | 500 | 3 | 55.16 | 78.52 | 10.52 |
| 2 (g) | 3-dimethylamino-1-propanol (3.4) | 9.2 | 200 | 3800 | 5 | 51.60 | 60.40 | 6.51 |
| 10 (g) | 2-dimethylamino ethanol (9.8) | 40 | 1 (g) | 15 (g) | 4 | 49.70 | 72.00 | 13.52 |

The aminoalcohols used in the process of enzymatic tiansesterification in object give substantially comparable conversions and enantiomeric excesses.

EXAMPLE 4

Resolution of Racemic Trans methyl 3-(4-methoxyphenyl)glycidate With 2-dimethylaminoethanol Changing the Temperature According to a procedure similar to the one reported in example 1, some trials of transesterification varying the system temperature were performed.

The obtained results and the corresponding experimental conditions are reported in the following table V:

TABLE V resolution of racemic trans methyl 3-(4-methoxyphenyl)glycidate changing the temperature

| Me-PGA (g) | 2-dimethyl amino ethanol(ml) | Toluene (ml) | Novozim 435°® (g) | Molec. sieves 5 Å (g) | Temp ° C. | Time (h) | c % | $ee_s$ % | E |
|---|---|---|---|---|---|---|---|---|---|
| 10 | 9.8 | 40 | 1 | 15 | 24 | 4 | 49.70 | 72.00 | 13.52 |
| 10 | 9.8 | 70 | 1 | 15 | 10 | 17 | 50.00 | 75.00 | 15.63 |

From the experimental data it is evident the maintenance of the enantioselectivity of the enzymatic preparation by changing the temperature.

EXAMPLE 5

Resolution of the methyl ester of Racemic Trans 3-(4-methoxyphenyl)glycidic acid in the Presence of Molecular Sieves The methyl ester of racemic trans 3-(4-methoxyphenyl) glycidic acid (10 g) was dissolved in toluene (34 g). Novozim 435® (1 g), ground molecular sieves 5 Å (15 g) and 2-dimethylaminoethanol (8.7 g) were successively added to the solution.

The suspension was kept under stirring for 3–4 hours at room temperature and then filtered under vacuum. The enzyme and the molecular sieves were washed with toluene (20 g) and the toluene phases collected.

The total toluene phase (54.9 g) contained the methyl ester of trans 3-(4-methoxyphenyl)glycidic acid (4.72 g, c=52.8%).

Water cooled at 0° C. (100 g) was added to the toluene solution and kept under stirring for 30 minutes. After phases separation, water cooled at 0° C. (80 g) and, slowly under stirring up to pH 6.8, a 85% solution of phosphoric acid (1.4 g) and water (20 g) were added to the organic phase.

The solution was kept under stirring for 1 hour, maintaining pH 6.8 by subsequent additions of the previously prepared phosphoric acid solution.

After having separated the phases, water cooled to 0° C. (80 g) and the phosphoric acid solution up to pH 6.8 were added to the toluene phase. It was left under stirring for 3 hours keeping the solution at pH 6.8 by adding the acid solution (20 g), it was separated the phases and it was extracted the aqueous phase with toluene.

The collected toluene phases contained the methyl ester of trans 3-(4-methoxyphenyl)glycidic acid (4.56 g), with a 2R,3S:2S,3R enantiomeric ratio of 90:10 (yield in the 2R,3S enantiomer equal to 82%).

The toluene solution was evaporated under reduced pressure, recovering 4.7 g of raw product.

The product was added with toluene (5 g), warmed at 50° C. up to complete dissolution, then the crystallisation was started by addition of a few crystals of the methyl ester of (2R,3S)-3-(4-methoxyphenyl)glycidic acid.

The mixture was cooled at 0° C. in 2 hours and kept at this temperature for 1 hour.

The precipitate was filtered, washed with toluene pre-cooled at 0° C. (1.7 g) and dried in oven at 60° C. under vacuum for 4 hours. There were obtained 3.1 g of product, with a 2R,3S:2S,3R enantiomeric ratio of 99:1 (crystallisation yield in the 2R,3S enantiomer equal to 75%).

EXAMPLE 6

Resolution of Racemic Trans methyl 3-(4-methoxyphenyl)glycidate With 2-dimethylaminoethanol Under Azeotropic Distillation Conditions The methyl ester of racemic trans 3-(4-methoxyphenyl) glycidic acid (12 g) was dissolved in toluene (58 ml). Novozim 435® (1g), 2-dimethylaminoethanol (12 ml) and methylcyclohexane (10 ml) were successively added to the solution.

The suspension was left under stirring for 4 hours, removing the azeotrope by under vacuum distillation (P=30 mmHg, T=25° C.) and restoring the evaporated solvents and 2-dimethylaminoethanol by subsequent additions (toluene 6 ml, methylcyclohexane 24 ml, 2-dimethylaminoethanol 12 ml).

It was carried out the isolation of the desired product similarly to what described in example 5, yielding the 2R,3S enantiomer with comparable yield and enantiomeric excess.

EXAMPLE 7

Resolution of Racemic Trans methyl 3-(4-methoxyphenyl)glycidate With 2-dimethylaminoethanol Using Recycled Novozim 435®

According to a procedure similar to the one reported in Example 6, some transesterification trials were performed in order to evaluate the stability of the enzyme when reused several times in subsequent reactions. After every reaction the enzyme was recovered by filtration, washed with toluene, dried in the air and at room temperature and used again in the subsequent reaction.

The following starting materials and conditions were employed:

| | |
|---|---|
| racemic trans methyl 3-(4-methoxyphenyl)glycidate (Me-PGA) | 12 g (15% w/v) |
| 2-dimethylaminoethanol (DMAE) | 12 ml |
| toluene | 58 ml |
| methylcyclohexane | 10 ml |
| Novozim 435 ® | 1 g |
| temperature | 25° C. |
| pressure | 30 mmHg |

The additional experimental variables and the obtained results were collected in the following table VI:

TABLE VI resolution of racemic trans methyl 3-(4-methoxyphenyl)glycidate using recycled Novozim 435 ®

| | Additions | | | | | | |
|---|---|---|---|---|---|---|---|
| Cycle | DMAE | Toluene | Me-cyclo hexane | Time (h) | c % | ee$_s$ % | E |
| 1 | 18 ml 3 ml/h | 12 ml | 47 ml | 2 5 | 34.21 54.55 | 44.52 74.95 | 19.98 9.48 |
| 2 | 18 ml 3 ml/h | 15 ml | 54 ml | 2 4.5 7 | 33.45 50.46 59.85 | 41.39 71.28 82.73 | 15.47 11.87 8.62 |
| 3 | 18 ml 3 ml/h | 15.5 ml | 57 ml | 2 4.5 7 | 31.44 49.60 59.57 | 38.53 70.49 84.09 | 16.76 12.56 9.29 |
| 4 | 18 ml 3 ml/h | 19.5 ml | 57 ml | 2 4.5 7 | 31.13 49.62 59.20 | 38.07 70.68 83.07 | 16.92 12.67 9.16 |
| 5 | 18 ml 3 ml/h | 21 ml | 55 ml | 2 4.5 7 | 29.79 48.78 58.82 | 36.26 70.13 85.12 | 18.16 13.64 10.29 |
| 6 | 18 ml 3 ml/h | 15 ml | 52 ml | 2 4.5 7 | 28.56 47.47 57.21 | 34.79 67.14 83.00 | 20.23 13.50 10.72 |

On the basis of the steady values of the conversion extent and the enantiomeric excess it can be concluded that the used enzymatic system was characterised by a high stability and that it can therefore be reused in more subsequent cycles, maintaining the same efficiency.

What we claim is:

1. A process for the preparation of:

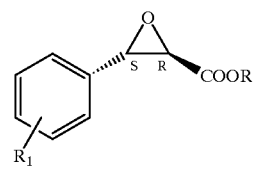

(I)

which comprises the enzymatic kinetic resolution of trans 3-phenylglycidates of formula:

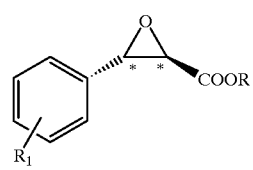

trans (I)

wherein

R is linear or branched $C_1$–$C_4$alkyl;

$R_1$ is hydrogen, linear or branched $C_1$–$C_3$ alkyl, linear or branched $C_1$–$C_3$ alkoxy, aryl or halogen;

by transesterification of the mixture of trans enantiomers of formula I catalysed by enzymes in organic solvent with aminoalcohols of formula:

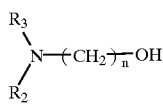

(II)

wherein
n is an integer from 2 to 4;
$R_2$ is hydrogen or linear or branched $C_1$–$C_4$ alkyl;
$R_3$ is linear or branched $C_1$–$C_4$ alkyl; or
$R_2$ and $R_3$ together with the nitrogen atom form a 5 to 7 membered saturated cycle;
to give a mixture of trans esters, non transesterified and transesterified, having an opposite absolute configuration, of formula III and IV respectively:

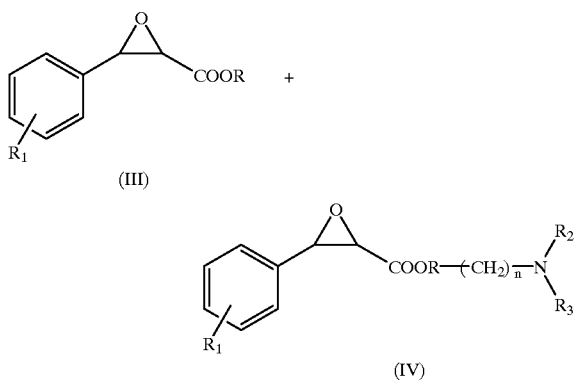

wherein R, $R_1$, $R_2$, $R_3$ and n have the above reported meanings,
and the subsequent separation of such a mixture of esters of formula III and IV.

2. A process according to claim 1 in which R is methyl.

3. A process according to claim 1 in which the aminoalcohol of formula II is selected among 3-dimethylamino-1-propanol, 2-diethylaminoethanol, 2-dimethylamino ethanol, 2-methylaminoethanol, 1-(2-hydroxyethyl)piperidine, 1-(2-hydroxyethyl)pyrrolidine.

4. A process according to claim 3 in which the aminoalcohol of formula II is 2-dimethylaminoethanol.

5. A process according to claim 1 in which the molar ratio between aminoalcohol (II) and trans 3-phenylglycidate (I) is comprised between 20:1 and 0.4:1.

6. A process according to claim 5 in which the molar ratio between aminoalcohol (II) and trans 3-phenylglycidate (I) is 2:1.

7. A process according to claim 1 in which the enzyme is a lipase selected among lipase from *Candida antarctica*, lipase from *Mucor miehei*, pancreatic porcine lipase, lipase from *Candida cylindiacea*, lipase from wheat germ, lipase from *Chromobacterium viscosum*, lipase from *Aspergillius niger*, lipase from *Rhizopus javanicus*, lipase from *Pennicillium cyclopium*, lipase from *Rhizopus delemar*, lipase from *Candida lipolytica*, lipase from *Pennicilium roquefortii*, lipase from *Humicola lanuginosa*, lipase from *Geotrichum candidum*, lipase from *Pseudomonas cepacea*, lipase from *Rhizopus japonicus* and lipase from *Peudomonas fluorescens*, optionally supported.

8. A process according to claim 7 in which the enzyme is the supported lipase from *Candida antarctica*.

9. A process according to claim 1 that also comprises the recovery of the enzyme at the end of the reaction and its optional reusing in the subsequent cycle.

10. A process according to claim 1 in which the organic solvent is selected among aromatic solvents, hydrocarbons, ethers, ketones, alcohols, aprotic dipolar solvents, chlorinated, or admixtures thereof.

11. A process according to claim 10 in which the organic solvent is selected among benzene, chlorobenzene, xylene, toluene, n-hexane, cyclohexane, n-heptane, diethylether, diisopropylether, ter-butylmethylether, tetrahydrofuran, dioxane, methylethylketone, acetone, ter-butanol, 2-methyl-2-butanol, acetonitrile, methylene chloride or admixtures thereof.

12. A process according to claim 11 in which the reaction solvent is toluene.

13. A process according to claim 1 in which the alcohol ROH released from the transesterification reaction is removed with molecular sieves.

14. A process according to claim 1 in which the alcohol ROH released from the transesterification reaction is removed by azeotropic distillation, in the presence of a suitable co-solvent.

15. A process according to claim 1 in which the transesterified IV and non-transesterifed III esters are separated by acid aqueous extraction.

16. A process according to claim 1 for the preparation of methyl(2R,3S)-3-(4-methoxyphenyl)glycidate.

17. A process for the preparation of diltiazem comprising preparing the compound (I) of claim 1 by the enzymatic kinetic resolution of trans 3-phenylglycidates in accordance with claim 1.

* * * * *